(12) United States Patent
Singal et al.

(10) Patent No.: US 10,130,815 B2
(45) Date of Patent: *Nov. 20, 2018

(54) AUTOMATIC THERAPY ADJUSTMENTS

(71) Applicant: Medtronic, Inc., Minneapolis, MN (US)

(72) Inventors: Ruchika Singal, Boulder, CO (US); Steven L. Jensen, Andover, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 580 days.

This patent is subject to a terminal disclaimer.

(21) Appl. No.: 13/764,054

(22) Filed: Feb. 11, 2013

(65) Prior Publication Data

US 2013/0150921 A1   Jun. 13, 2013

Related U.S. Application Data

(63) Continuation of application No. 10/691,917, filed on Oct. 23, 2003, now Pat. No. 8,396,565.

(Continued)

(51) Int. Cl.
*A61N 1/36* (2006.01)
*A61N 1/372* (2006.01)
(Continued)

(52) U.S. Cl.
CPC ..... *A61N 1/36071* (2013.01); *A61N 1/36135* (2013.01); *A61N 1/37264* (2013.01);
(Continued)

(58) Field of Classification Search
CPC ................................................. A61N 1/36535
(Continued)

(56) References Cited

U.S. PATENT DOCUMENTS 4,297,685 A   10/1981   Brainard, II
4,365,633 A   12/1982   Loughman
(Continued)

FOREIGN PATENT DOCUMENTS

DE   19831109   1/2000
DE   10024103   11/2001
(Continued)

OTHER PUBLICATIONS

Office Action from U.S. Appl. No. 12/966,827 dated Dec. 4, 2013, 10 pp.
(Continued)

*Primary Examiner* — Alyssa M Alter
(74) *Attorney, Agent, or Firm* — Shumaker & Sieffert, P.A.

(57) ABSTRACT

A medical device detects a previously defined event, and controls delivery of therapy to a patient according to therapy information associated with the previously defined event. In exemplary embodiments, the medical device enters a learning mode in response to a command received from a user, e.g., the patient or a clinician. In such embodiments, the medical device defines the event, collects the therapy information, and associates the therapy information with the defined event while operating in the learning mode. In some embodiments, the medical device defines the event based on the output of a sensor that indicates a physiological parameter of the patient during the learning mode. The sensor may be an accelerometer, which generates an output that reflects motion and/or posture of the patient. The medical device may collect therapy information by recording therapy changes made by the user during the learning mode.

41 Claims, 8 Drawing Sheets

Related U.S. Application Data

(60) Provisional application No. 60/503,218, filed on Sep. 15, 2003.

(51) Int. Cl.
*A61B 5/11* (2006.01)
*A61N 1/365* (2006.01)

(52) U.S. Cl.
CPC ............ *A61B 5/1116* (2013.01); *A61B 5/1118* (2013.01); *A61N 1/36132* (2013.01); *A61N 1/36139* (2013.01); *A61N 1/36535* (2013.01); *A61N 1/36542* (2013.01)

(58) Field of Classification Search
USPC ..................................................... 607/17, 48
See application file for complete search history.

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A * | 10/1991 | Bourgeois .............. A61N 1/372 607/46 |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A * | 1/1997 | Sheldon .......................... 607/19 |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,716,377 A | 2/1998 | Rise et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,044,297 A | 3/2000 | Sheldon et al. |
| 6,083,475 A | 3/2000 | Sikorski et al. |
| 6,045,513 A | 4/2000 | Stone et al. |
| 6,059,576 A | 5/2000 | Brann |
| 6,081,750 A | 6/2000 | Hoffberg et al. |
| 6,095,991 A | 8/2000 | Krausman et al. |
| 6,099,479 A | 8/2000 | Christopherson et al. |
| 6,102,874 A | 8/2000 | Stone et al. |
| 6,120,467 A * | 9/2000 | Schallhorn .................... 600/595 |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |

(56) References Cited

U.S. PATENT DOCUMENTS

| | | |
|---|---|---|
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Miesel et al. |
| 7,853,322 B2 | 12/2010 | Bourget et al. |
| 7,957,797 B2 | 6/2011 | Bourget et al. |
| 7,957,809 B2 | 6/2011 | Bourget et al. |
| 8,396,565 B2 * | 3/2013 | Singhal et al. ............ 607/116 |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 * | 11/2002 | Pless ............... A61M 5/14276 607/48 |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0043772 A1 * | 2/2005 | Stahmann ............ A61N 1/36514 607/42 |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |

(56) References Cited

U.S. PATENT DOCUMENTS

| | | |
|---|---|---|
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0233201 A1 | 10/2007 | Lovett et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | Kristofer et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |
| 2011/0082522 A1 | 4/2011 | Bourget et al. |
| 2011/0238130 A1 | 9/2011 | Bourget et al. |
| 2011/0238136 A1 | 9/2011 | Bourget et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 0613390 | 10/2000 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/87433 | 11/2002 |
| WO | 02/96512 | 12/2002 |
| WO | 02/100267 | 12/2002 |
| WO | 03/51356 | 6/2003 |
| WO | 03/65891 | 8/2003 |
| WO | 05/28029 | 3/2005 |
| WO | 05/35050 | 4/2005 |
| WO | 05/79487 | 9/2005 |
| WO | 05/89646 | 9/2005 |
| WO | 05/89647 | 9/2005 |
| WO | 05/89860 | 9/2005 |
| WO | 05/102499 | 11/2005 |
| WO | 05/120348 | 12/2005 |
| WO | 07/09088 | 1/2007 |
| WO | 07/51196 | 5/2007 |
| WO | 07/64682 | 6/2007 |
| WO | 07/64936 | 6/2007 |
| WO | 08/26970 | 3/2008 |

OTHER PUBLICATIONS

Office Action from U.S. Appl. No. 13/154,303 dated Dec. 5, 2013, 7 pp.

(56) References Cited

OTHER PUBLICATIONS

"Analysis of heart rate dynamics by methods derived from nonlinear mathematics: Clinical applicability and prognostic significance," http://herkules.oulu.fi.isbn9514250133/html, 4 pp., 2004.
"Design Competition: Runners-Up for the Best Three Designs," EPN, vol. 26, No. 1, 1 pg., 2002.
"IBM and Citizen Watch develop Linux-Based WatchPad," http://wwwlinuxdevices.com.news/NS6580187845.html, 5 pp., 2006.
"MiniMitter® Physiological and Behavioral Monitoring for Humans and Animals," http://www.minimitter.com/Products/Actiwatch, 3 pp., 2006.
"Watch," Wikipedia, 6 pp., http://en.wikipedia.org/wiki/Watch, 2006.
Aminian et al., "Physical Activity Monitoring Based on Accelerometry: Validation and Comparison with Video Observation," Medical & Biological Engineering and Computing, vol. 37, No. 2, pp. 304-308, 1999.
Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.
Ang et al., "Physical model of a MEMS accelerometer for low-g motion tracking applications," 2004 IEEE International Conference on Robotics and Automation, vol. 2, pp. 1345-1351, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006, 5 pp., http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, 9$^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp., 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Continuous Monitoring of Upper Limb Activity in a Free-Living Environment," Arch Phys Med Rehabil, vol. 86, pp. 541-548, Mar. 2005.
Leung et al., "An Integrated Dual Sensor System Automatically Optimized by Target Rate Histogram," Pacing and Clinical Electrophysiology, vol. 21, No. 8, 7 pp. Aug. 8, 1998.
Saoudi et al., "How Smart Should Pacemakers Be?," American Journal of Cardiology, vol. 83, No. 5, 6 pp., Mar. 5, 1999.

(56) References Cited

OTHER PUBLICATIONS

Velten et al., "A New Three-Axis Accelerometer," Sensor '99-9$^{th}$ Int'l Trade Fair and Conference for Sensors/Transducers & Systems, Nurnberg, Germany, May 18-20, 1999, Sensor '99 Proceedings II, 1999, A 5.2, 6 pp.
International Preliminary Report on Patentability for PCT Application PCT/US2004/002113, dated Sep. 19, 2005, 5 pp.
European Office Action dated Nov. 13, 2008 for Application No. 06844740.8, 2 pp.
European Office Action dated Nov. 13, 2008 for Application No. 06844725.9, 2 pp.
Canadian Office Action dated Mar. 12, 2012 for Canadian Application No. 2,538,356, 3pp.
Prosecution History from U.S. Pat. No. 8,396,565 from Feb. 28, 2006 through Jan. 11, 2013, 263 pp.
Prosecution History from U.S. Pat. No. 7,853,322 from Jul. 23, 2008 through Sep. 15, 2010, 139 pp.
Prosecution History from U.S. Pat. No. 7,957,809 from Mar. 9, 2010 through Jan. 31, 2011, 37 pp.
Prosecution History from U.S. Pat. No. 7,957,797 from Mar. 9, 2010 through Jan. 31, 2011, 58 pp.
Prosecution History from U.S. Appl. No. 12/966,827, filed Jul. 10, 2012 through Nov. 15, 2013, 48 pp.
Prosecution History from U.S. Appl. No. 13/154,303, filed Aug. 16, 2013 through Nov. 15, 2013, 14 pp.
Prosecution History from U.S. Appl. No. 13/154,309, filed Nov. 23, 2012 through Nov. 1, 2013, 41 pp.
Notice of Allowance from U.S. Appl. No. 13/154,309, dated Jan. 8, 2014, 7 pp.
Response to Office Action dated Dec. 5, 2013 from U.S. Appl. No. 13/154,303, filed Mar. 5, 2014, 8 pp.
Office Action from U.S. Appl. No. 13/154,303, dated Jul. 7, 2014, 7 pp.
Notice of Allowance from U.S. Appl. No. 12/966,827, dated Jul. 18, 2014, 5 pp.
Response to Office Action dated Jul. 7, 2014, from U.S. Appl. No. 13/154,303, filed Oct. 7, 2014, 8 pp.
Final Office Action from U.S. Appl. No. 13/154,303, dated Dec. 11, 2014, 8 pp.
Response to Final Office Action dated Dec. 11, 2014, from U.S. Appl. No. 13/154,303, filed Feb. 11, 2015, 4 pp.
Examiners Answer from U.S. Appl. No. 13/154,303, dated Nov. 9, 2015, 9 pp.
Response to Decision on Appeal dated Oct. 2, 2017, from U.S. Appl. No. 13/154,303, filed Dec. 4, 2017, 9 pp.
Decision on Appeal from U.S. Appl. No. 13/154,303, dated Oct. 2, 2017, 16 pp.
Written Opinion from International Application No. PCT/US2004/002113, dated Jun. 21, 2004, 5 pp.
Response to Examiner's second report from counterpart Australian Patent Application No. 2004279285, filed on Aug. 10, 2010, 2 pp.
Examiners Report from counterpart Canadian Patent Application No. 2538356, dated Mar. 21, 2013, 3 pp.
Response to Examiner's Report dated Mar. 12, 2012, from counterpart Canadian Patent Application No. 2538356, filed on Sep. 11, 2012, 16 pp.
Response to Examiner's Report dated Mar. 21, 2013, from counterpart Canadian Patent Application No. 2538356, filed on Jul. 8, 2013, 10 pp.
Examiners Report from counterpart Canadian Patent Application No. 2538356, dated Feb. 3, 2011, 2 pp.
Response to Examiner's Report dated Feb. 3, 2011, from counterpart Canadian Patent Application No. 2538356, filed on Jun. 21, 2011, 9 pp.
Office Action from US. Appl. No. 13/154,303, dated Jan. 12, 2018, 9 pp.
Response to Office Action dated Jan. 12, 2018, from U.S. Appl. No. 13/154,303, filed Apr. 12, 2018, 6 pp.
Office Action from U.S. Appl. No. 13/154,303, dated Aug. 16, 2018, 9 pp.

\* cited by examiner

AUTOMATIC THERAPY ADJUSTMENTS

This application is a continuation of, and claims priority to, U.S. application Ser. No. 10/691,917 filed Oct. 23, 2003, issued as U.S. Pat. No. 8,396,565 B2 on Mar. 12, 2013, which claims priority to U.S. Provisional Application Ser. No. 60/503,218, filed Sep. 15, 2003, the entire content of both of which are incorporated herein by reference.

TECHNICAL FIELD

The invention relates to medical devices, and more particularly, to medical devices used for chronic therapy provision.

BACKGROUND

A variety of types of medical devices are used for chronic, e.g., long-term, provision of therapy to patients. As examples, pulse generators are used for chronic provision of cardiac pacing and neurostimulation therapies, and pumps are used for chronic delivery of therapeutic agents, such as drugs. Typically, such devices provide therapy continuously or periodically according to parameters, e.g., a program, specified by a clinician.

In some cases, the patient is allowed to activate and/or modify the therapy. For example, the symptoms, e.g., the intensity of pain, of patients who receive spinal cord stimulation (SCS) therapy may vary over time based on the activity level or posture of the patient, the specific activity undertaken by the patient, or the like. For this reason, a patient who receives SCS therapy from an implantable medical device (IMD), e.g., an implantable pulse generator, is often given a patient programming device that communicates with his IMD via device telemetry, and allows the patient to activate and/or adjust the intensity of the delivered neurostimulation.

SUMMARY

In general, the invention is directed to techniques for providing automatic adjustments to a therapy. A medical device, such as an implanted medical device (IMD) for delivering a therapy or a programming device, automatically adjusts delivery of the therapy in response to detecting a previously defined event. By automatically adjusting therapy in response to detecting a previously defined event, the medical device can automatically provide appropriate therapy to address changes in the symptoms of a patient, and/or changes in the efficacy or side effects of the therapy associated with the event. The medical device may deliver neurostimulation therapy, and an event may be an activity and/or posture undertaken by the patient, such as running or sitting in a chair, which will likely impact the type or level of symptoms and/or the paresthesia experienced by the patient.

In exemplary embodiments, the medical device enters a learning mode in response to a command received from a user, e.g., the patient. In such embodiments, the medical device defines the event, collects the therapy information, and associates the therapy information with the defined event while operating in the learning mode. In some embodiments, the medical device defines the event based on an indication of the event received from the user. In other embodiments, the medical device defines the event based on the output of a sensor that indicates the activity, posture, or a physiological parameter of the patient during the learning mode. The sensor may be an accelerometer, which generates an output that reflects motion and/or posture of the patient. The medical device may collect therapy information by recording values of one or more therapy parameters, such as pulse amplitude, width and rate, and/or changes made to the parameters by the user during the learning mode.

When a patient undertakes certain activities and/or postures, the patient may experience an uncomfortable increase in the intensity of the neurostimulation delivered by a medical device. This phenomenon is referred to as a "jolt." Some of the events detected by the medical device may correspond to a jolt. In response to detecting these events, the medical device may suspend delivery of neurostimulation therapy for a period of time, which may advantageously allow the medical device avoid providing uncomfortable stimulation to the patient.

In one embodiment, the invention is directed to a method in which a command to enter a learning mode is received from a user. An event is defined, and therapy information is associated with the defined event, in response to the command. The defined event is subsequently detected, and therapy is provided to a patient via a medical device according to the therapy information in response to the detection.

In another embodiment, the invention is directed to a medical device that comprises a memory and a processor. The processor receives a command to enter a learning mode from a user, and defines an event and associates therapy information with the defined event within the memory in response to the command. The processor subsequently detects the event, and controls delivery of therapy to a patient according to the therapy information in response to the detection.

In another embodiment, the invention is directed to a computer-readable medium containing instructions. The instructions cause a programmable processor to receive a command from a user to enter a learning mode, and define and event and associate therapy information with the defined event in response to the command. The computer-readable medium further comprises instructions that cause a programmable processor to subsequently detect the defined event, and control delivery of therapy to a patient via a medical device according to the therapy information in response to the detection.

The invention may provide advantages. For example, by automatically adjusting therapy in response to a detected event, a medical device can provide therapy that better addresses changes in the symptoms of a patient and/or level of efficacy or side effects of the therapy associated with an activity undertaken by the patient. The medical device may automatically provide the appropriate therapy for frequently occurring events, e.g., activities that the patient frequently undertakes, allowing the patient to avoid having to manually adjust the therapy each time the event occurs. Manual adjustment of stimulation parameters can be tedious, requiring the patient to, for example, depress one or more keys of a keypad of a patient programmer multiple times during the event to maintain adequate symptom control. Instead, according to the invention, the patient may perform such adjustments a single time during a learning mode, and the medical device may automatically provide the adjustments during subsequent occurrences of the event.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
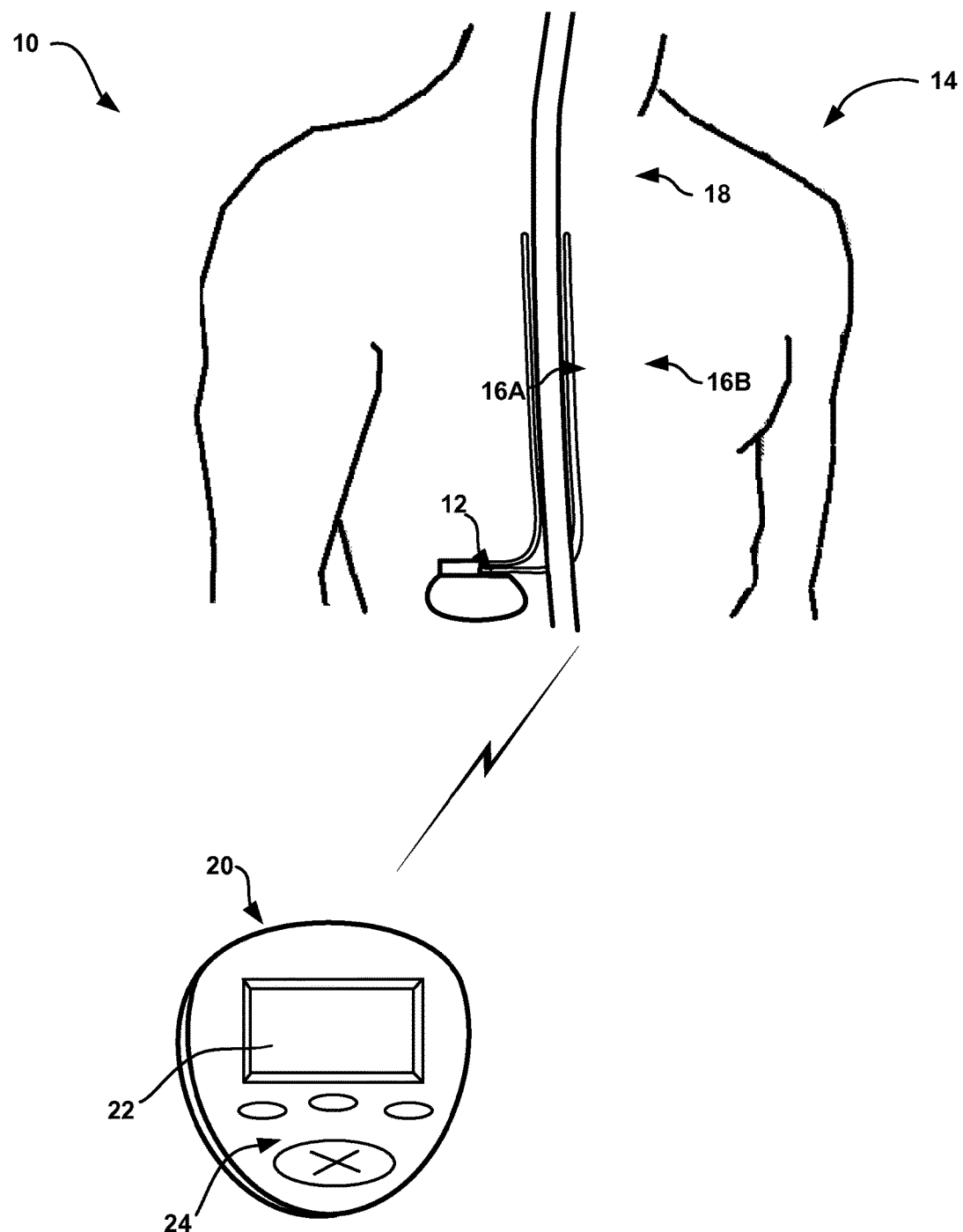
FIG. 1 is a conceptual diagram illustrating an exemplary system that facilitates automatic discrete therapy adjustment according to the invention.

FIG. 1 is a conceptual diagram illustrating an exemplary system 10 that facilitates automatic therapy adjustment according to the invention. In the illustrated example, system 10 includes an implantable medical device (IMD) 12, which is implanted within a patient 14, and delivers neurostimulation therapy to patient 14. In exemplary embodiments, IMD 12 takes the form of an implantable pulse generator, and delivers neurostimulation therapy to patient 14 in the form of electrical pulses.

IMD 12 delivers neurostimulation therapy to patient 14 via leads 16A and 16B (collectively "leads 16"). Leads 16 may, as shown in FIG. 1, be implanted proximate to the spinal cord 18 of patient 14, and IMD 12 may deliver spinal cord stimulation (SCS) therapy to patient 14 in order to, for example, reduce pain experienced by patient 14. However, the invention is not limited to the configuration of leads 16 shown in FIG. 1 or the delivery of SCS therapy. For example, one or more leads 16 may extend from IMD 12 to the brain (not shown) of patient 14, and IMD 12 may deliver deep brain stimulation (DBS) therapy to patient 14 to, for example, treat tremor or epilepsy. As further examples, one or more leads 16 may be implanted proximate to the pelvic nerves (not shown) or stomach (not shown), and IMD 12 may deliver neurostimulation therapy to treat incontinence or gastroparesis.

In exemplary embodiments, IMD 12 delivers therapy to patient 14 according to a program. A program includes one or more parameters that define an aspect of the therapy delivered by the medical device according to that program. For example, a program that controls delivery of neurostimulation by IMD 12 may define a voltage or current pulse amplitude, a pulse width, a pulse rate, for stimulation pulses delivered by IMD 12 according to that program. Further, each of leads 16 includes electrodes (not shown in FIG. 1), and the parameters for a program that controls delivery of neurostimulation therapy by IMD 12 may include information identifying which electrodes have been selected for delivery of pulses according to the program, and the polarities of the selected electrodes.

In the illustrated example, system 10 also includes a programming device 20, which is a medical device, and may, as shown in FIG. 1, be a handheld computing device. Programming device 20 allows a user to interact with IMD 12. Programming device 20 may, for example, communicate via wireless communication with IMD 12 using RF telemetry techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions.

In exemplary embodiments, programming device 20 is a patient programmer used by patient 14 to control the delivery of neurostimulation therapy by IMD 12. Patient 14 may use programming device 20 to activate or deactivate neurostimulation therapy. Patient 14 may also use programming device 20 to adjust one or more program parameters, e.g., adjust the amplitude, width, or rate of delivered stimulation pulse. Where more than one program is available to IMD 12 for delivery of neurostimulation to patient 14, patient 14 may use programming device 20 to select from among the available programs. The programs available for selection by patient 14 may be stored in either of IMD 12 and programming device 20.

As will be described in greater detail below, one or both of IMD 12 and programming device 20 provide automatic adjustment of the therapy delivered by IMD 12 according to the invention. Specifically, one of IMD 12 and programming device 20 detects a previously defined event, and the delivery of therapy by IMD 12 is automatically adjusted according to therapy information stored in association with defined event. In exemplary embodiments, the one of IMD 12 and programming device 20 may make automatic adjustments to the therapy over a period of time in response to detection of the previously defined event, e.g., provide a series of therapy adjustments defined by the therapy information associated with the event. By automatically adjusting therapy in response to a detected event, system 10 can provide therapy that better addresses changes in the symptoms of patient 14 associated with the event.

For ease of description, the provision of automatic therapy adjustment will be described hereinafter primarily with reference to embodiments in which IMD 12 provides automatic therapy adjustments. However, it is understood that both of IMD 12 and programming device 20 are medical devices capable of providing automatic therapy adjustments according to the invention.

In exemplary embodiments, IMD 12 provides a learning mode. IMD 12 may enter the learning mode in response to a command received from a user. For example, patient 14 may direct IMD 12 to enter the learning mode via keypad 24 of patient programmer 20.

When operating in the learning mode, IMD 12 defines events and associates therapy information with the events. In some embodiments, IMD 12 defines the event based on the indication of the event to IMD 12 by a user. In such embodiments, IMD 12 later detects the event by receiving the indication from the user, and automatically adjusts therapy according to information stored in association with that indication, e.g., with the event.

For example, patient 14 may indicate the occurrence of an event to IMD 12 via keypad 24 of patient programmer 20.

In some embodiments, a particular key of keypad 24 is associated with the event. The event may correspond to an activity undertaken by patient 14, such as running, golfing, taking medication, sleeping, or a particular activity related to an occupation of patient 14. A first time patient 14 undertakes the activity, the activity, e.g., event, may be associated with a key of keypad 24. Subsequent times patient 14 undertakes the activity, patient 14 may press the key to cause IMD 12 to provide therapy adjustment according to therapy information associated with depression of the key.

In other embodiments, IMD 12 defines the event based on the output of a sensor (not shown in FIG. 1). IMD 12 may monitor the sensor output in response to the command to enter the learning mode received from the user, e.g., patient 14. After the event is defined, IMD 12 may monitor the output of the sensor, and, if the event is subsequently detected, provide automatic therapy adjustment according to information stored in association with the event. For example, IMD 12 may record the sensor output for a period during the learning mode to define the event, and, when no longer operating in the learning mode, apply digital signal and/or pattern recognition analysis techniques to the sensor output to automatically identify subsequent occurrences of the event based on comparison to the recorded exemplar.

The output of the sensor may reflect motion, posture, and/or one or more physiological parameters of patient 14. Consequently, events defined by IMD 12 based on the sensor output may correspond to an activity undertaken by patient 14. For example, patient 14 may direct IMD 12 to enter the learning mode via patient programmer 20 when patient 14 is about to undertake an activity, such as running IMD 12 may record the output of the sensor in response to the command, and, when no longer in the learning mode, use the recorded exemplar to detect when patient 14 is running so as to automatically provide an appropriate therapy adjustment according to therapy information stored in association with the exemplar.

IMD 12 may associate therapy information with the defined event while operating in the learning mode, and provide therapy, e.g., automatically adjusts the therapy, according to the therapy information in response to subsequent detection of the defined event. The therapy information may be the values of one or more parameters, e.g., pulse amplitude, pulse width, or pulse rate, recorded by IMD 12 upon entering, or at some point after entering, the learning mode. The therapy information may be a change to a parameter made by a user while IMD 12 is operating in the learning mode. In exemplary embodiments, IMD 12 records a series of changes made to parameters by the user over a period of time while IMD 12 is operating in the learning mode.

For example, patient 14 may direct IMD 12 to enter the learning mode so that IMD 12 will learn the appropriate adjustment or adjustments to make to the stimulation parameters while patient 14 is running. Patient 14 may indicate the occurrence of the event to IMD 12, e.g., may associate a key of keypad 24 with the activity of running, or may simply begin running and allow IMD 12 to record an exemplar of the sensor output while patient 14 is running. In any case, while patient 14 is running during the learning mode, patient 14 uses programming device 20, e.g., keypad 24, to change one or more stimulation parameters in an attempt to maintain adequate symptom control during the activity. IMD 12 may record the value of the parameters when patient 14 indicates satisfaction, or the one or more changes made by patient 14 over a period of time while running IMD 12 stores the values or a recording of the changes over the time period in association with the event, and, when no longer operating in the learning mode, delivers therapy according to the therapy information upon subsequently detecting that patient 14 is running.

By associating therapy information with defined events, IMD 12 may automatically provide appropriate therapy to patient 14 for frequently occurring events, e.g., activities that patient 14 frequently undertakes. By providing therapy adjustments automatically, IMD 12 may allow patient 14 to avoid having to manually adjust the therapy each time the event occurs. Such manual adjustment of stimulation parameters can be tedious, requiring patient 14 to, for example, depress one or more keys of keypad 24 multiple times during the event to maintain adequate symptom control. Instead, according to the invention, patient 14 may perform such adjustments a single time during the learning mode, and IMD 12 may automatically provide the adjustments during subsequent occurrences of the event.

Figure 2:
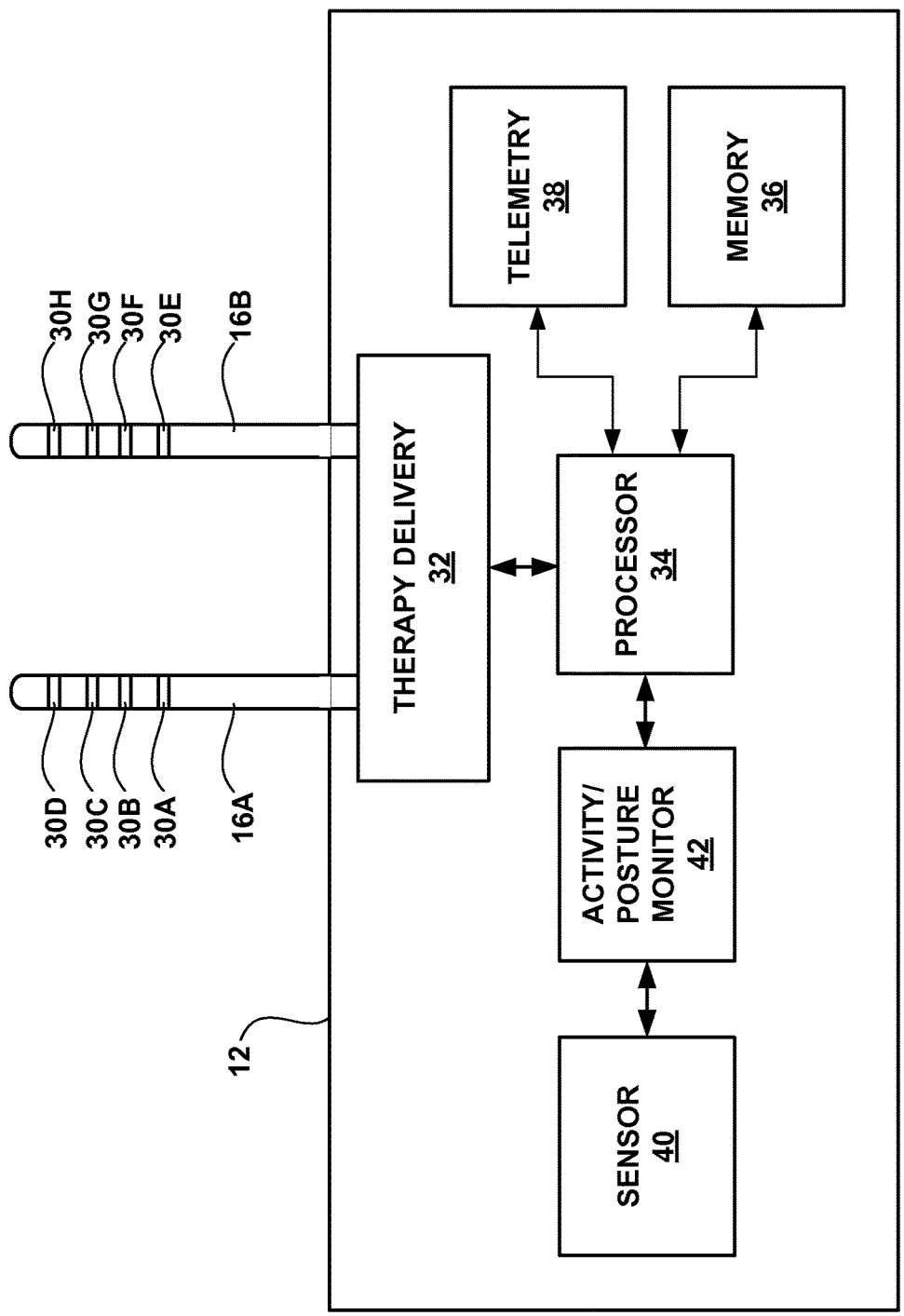
FIG. 2 is a block diagram illustrating an example medical device that provides therapy and automatically makes discrete adjustments to the therapy.

FIG. 2 is a block diagram illustrating IMD 12 in greater detail. IMD 12 may deliver neurostimulation therapy via electrodes 30A-D of lead 16A and electrodes 30E-H of lead 16B (collectively "electrodes 30"). Electrodes 30 may be ring electrodes. The configuration, type and number of electrodes 30 illustrated in FIG. 2 are merely exemplary.

Electrodes 30 are electrically coupled to a therapy delivery circuit 32 via leads 16. Therapy delivery circuit 32 may, for example, include an output pulse generator coupled to a power source such as a battery. Therapy delivery circuit 32 may deliver electrical pulses to patient 14 via at least some of electrodes 30 under the control of a processor 34.

Processor 34 may control therapy delivery circuit 32 to deliver neurostimulation therapy according to a selected program. Specifically, processor 34 may control circuit 32 to deliver electrical pulses with the amplitudes and widths, and at the rates specified by the program. Processor 34 may also control therapy delivery circuit 32 to deliver the pulses via a selected subset of electrodes 40 with selected polarities, as specified by the program.

Processor 34 may also provide a learning mode of IMD 12 as described above. Specifically, processor 34 may receive commands from a user to enter the learning mode, may define an event during the learning mode, and may associate therapy information with the defined event within memory 36, as described above. When processor 34 is no longer operating in the learning mode, processor 34 and/or monitor 42 may detect previously defined events, and control therapy delivery circuit 32 to deliver therapy via at least some of electrodes 30 as indicated by the associated therapy information. Specifically, processor 34 may control therapy delivery circuit to deliver stimulation pulses with the amplitude, width, and rate indicated by the therapy information, and, in some embodiments, may control therapy delivery circuit to adjust the amplitude, width, and/or rate over time as indicated by the therapy information.

IMD 12 also includes a telemetry circuit 38 that allows processor 34 to communicate with programming device 20. Processor 34 may receive program selections, commands to enter a learning mode, indications of events, and adjustments to therapy made by a user, e.g., patient 14, using programming device 20 via telemetry circuit 38. In some embodiments, as will be described in greater detail below, processor 34 communicates with a clinician programmer to provide diagnostic information stored in memory 36 to a clinician via telemetry circuit 38. Telemetry circuit 38 may correspond to any telemetry circuit known in the implantable medical device arts.

In exemplary embodiments, as described above, IMD 12 includes a sensor 40, and processor 34 defines events based on the output of sensor 40. Sensor 40 is a sensor that generates an output based on motion, posture, and/or one or more physiological parameters of patient 14. In exemplary embodiments, sensor 40 is an accelerometer, such as a piezoresistive and/or micro-electro-mechanical accelerometer.

In some embodiments, IMD 12 includes an activity/posture monitor 42 that processes the analog output of sensor 40 to provide digital activity and/or posture information to processor 34. For example, where sensor 40 comprises a piezoresistive accelerometer, monitor 42 may process the raw signal provided by sensor 40 to provide activity counts to processor 34. In some embodiments, IMD 12 includes multiple sensors oriented along various axes, or sensor 40 comprises a single multi-axis, e.g., three-axis, accelerometer. In such embodiments, monitor 42 may process the signals provided by the one or more sensors 40 to provide velocity of motion information for each direction to processor 34.

In exemplary embodiments, the one or more sensors 40 are housed within a housing (not shown) of IMD 12. However, the invention is not so limited. In some embodiments, one or more sensors 40 are coupled to monitor 42 housed within IMD 12 via additional leads 16 (not shown). Such sensors may be located anywhere within patient 14. In some embodiments, IMD 12 may include multiple accelerometer sensors 40 located at various positions within patient 14 or on the external surface of patient 14, and processor 34 may receive more detailed information about the posture of and activity undertaken by patient 14. For example, accelerometer sensors 40 may be located within the torso and at a position within a limb, e.g. a leg, of patient 14.

Sensors 40 may be coupled to a single monitor 42, or IMD 12 may include multiple monitors 42 coupled to one or more sensors 40. Further, the invention is not limited to embodiments of IMD 12 that include a monitor 42. Rather, sensors 40 may be coupled directly to processor 34, which may include an analog-to-digital converter, and perform the functions attributed to monitor 42. In some embodiments, sensors located external to patient 12 may communicate wirelessly with processor 34, either directly or via programming device 20. In some embodiments, one or more sensors 40 may be included as part of or coupled to programming device 20.

Moreover, the invention is not limited to embodiments where sensors 40 are accelerometers. In some embodiments, one or more sensors 40 may take the form of, for example, a thermistor, a pressure transducer, or electrodes to detect thoracic impedance or an electrogram. Such sensors 40 may be appropriately positioned within or on an external surface of patient 14 to measure a physiological parameter of patient 14, such as a skin temperature, an arterial or intracardiac pressure, a respiration rate, a heart rate, or a Q-T interval of patient 14. In such embodiments, one or more monitor circuits 42 may provide appropriate circuitry to process the signals generated by such sensors, and to provide values of the physiological parameter to processor 34.

Processor 34 may include a microprocessor, a controller, a digital signal processor (DSP), an application specific integrated circuit (ASIC), a field-programmable gate array (FPGA), discrete logic circuitry, or the like. Memory 38 may include program instructions that, when executed by processor 34, cause IMD 12 to perform the functions ascribed to IMD 12 herein. Memory 36 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like.

Figure 3:
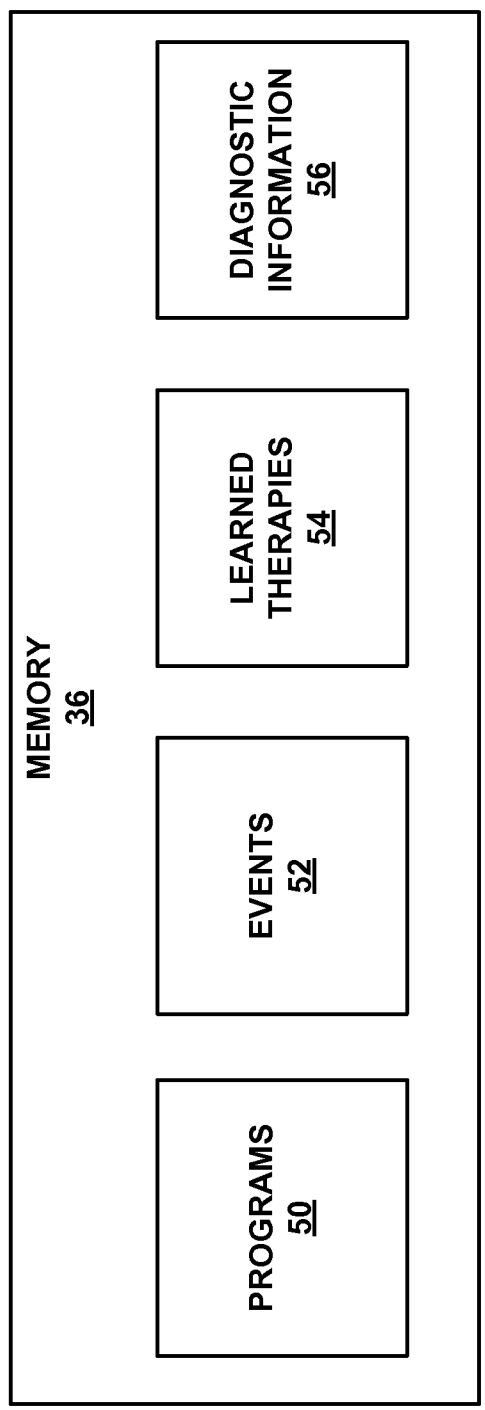
FIG. 3 is a block diagram illustrating an exemplary configuration of a memory of the medical device of FIG. 2.

FIG. 3 is a block diagram illustrating an exemplary configuration of memory 36 of IMD 12. In some embodiments, memory 36 stores the one or more programs 50 used by processor 34 (FIG. 2) to control delivery of stimulation by therapy delivery circuit 32 (FIG. 2). Processor 34 may receive the programs from a clinician via a clinician programming device and telemetry circuit 38 (FIG. 2), and store the programs in memory 36. In other embodiments, programs 50 are stored within a memory of programming device 20, and provided to processor 34 via telemetry circuit 38 as needed.

Memory 38 stores events 52 defined by processor 34 during operation in the learning mode, and learned therapies 54, i.e., the therapy information collected during operation in the learning mode. As described above, an event 52 may be information describing an event indication received from a user, e.g., patient 14 (FIG. 1), during the learning mode. For example, an event 52 may indicate a signal received via telemetry circuit 38 when patient presses a key of keypad 24 (FIG. 1) that patient 14 has associated with an activity undertaken by patient 14.

In some embodiments, as described above, processor 34 defines events 52 based on the output of one or more sensors 40. Processor 34 may store one or more sample of the output of sensor 40 and/or monitor 42 collected while operating in the learning mode as an event, or one or more results of an analysis such samples. For example, processor 34 may store information related to the detection of features within the one or more samples, such as peaks, zero-crossings, or the like, or the results of a Fourier or wavelet analysis of the one or more samples as a defined event 52.

As described above, learned therapies 54 comprises information describing values of stimulation parameters and/or information describing one or more changes to parameters made by a user while processor 34 is operating in the learning mode. In exemplary embodiments, a learned therapy 54 comprises information describing initial parameter values and changes to be made to some or all of the parameter values over a period of time. In such embodiments, the learned therapy may include time values associated with parameter values, so that processor 34 may direct changes to parameter values at appropriate times. Memory 36 maintains associations between events 52 and corresponding learned therapies 54.

Processor 34 may also collect diagnostic information 56 and store diagnostic information 56 within memory 36 for future retrieval by a clinician. Diagnostic information 56 may, for example, include selected recordings of the output of sensor 40 and/or of therapy changes made by patient 14. In exemplary embodiments, diagnostic information 56 includes information identifying the time at which defined events occurred, either during operation in a learning mode or as subsequently detected by processor 34. Diagnostic information 56 may include other information or events indicated by patient 14 outside of learning mode using programming device 20, such as changes in symptoms, taking medication, or other activities undertaken by patient 14 for which patient 14 does not wish IMD 12 to learn a therapy. A clinician programming device (not shown in FIGS.) may present diagnostic information 56 to a clinician in a variety of forms, such as timing diagrams, or a graph resulting from statistical analysis of diagnostic information 56, e.g., a bar graph.

Figure 4:
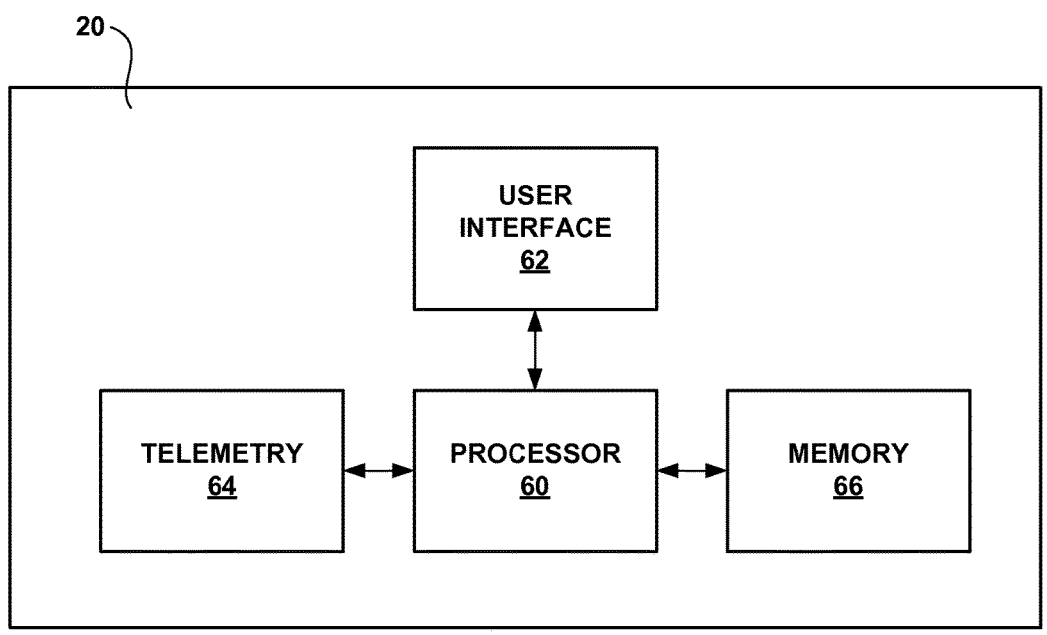
FIG. 4 is a block diagram illustrating an example programming device that allows a user to communicate with the medical device of FIG. 2.

FIG. 4 is a block diagram further illustrating programming device 20. As indicated above, in exemplary embodiments programming device 20 takes the form of a patient programming device used by patient 14 to control delivery of therapy by IMD 12. Patient 14 may interact with a processor 60 via a user interface 62 in order to control delivery of neurostimulation therapy, direct IMD 12 to enter a learning mode, indicate events and make therapy changes, as described herein. User interface 62 may include display 22 and keypad 24, and may also include a touch screen or peripheral pointing devices as described above. Processor 60 may also provide a graphical user interface (GUI) to facilitate interaction with patient 14. Processor 60 may include a microprocessor, a controller, a DSP, an ASIC, an FPGA, discrete logic circuitry, or the like.

Programming device 20 also includes a telemetry circuit 64 that allows processor 60 to communicate with IMD 12. In exemplary embodiments, processor 60 communicates commands, indications, and therapy changes made by patient 14 via user interface 62 to IMD 12 via telemetry circuit 64. Telemetry circuit 64 may correspond to any telemetry circuit known in the implantable medical device arts.

Programming device also includes a memory 66. In some embodiments, memory 66, rather than memory 36 of IMD 12, may store programs 50 that are available to be selected by patient 14 for delivery of neurostimulation therapy. Memory 66 may also include program instructions that, when executed by processor 60, cause programming device 20 to perform the functions ascribed to programming device 20 herein. Memory 66 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 5:
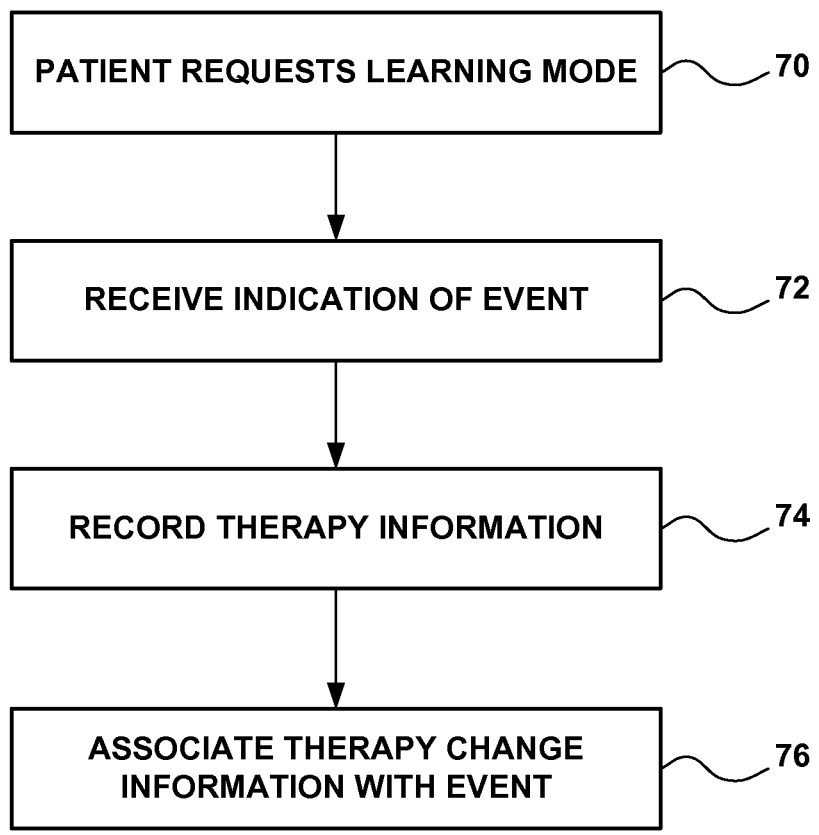
FIG. 5 is a flow diagram illustrating an exemplary operation of the medical device of FIG. 2 according to a learning mode.

FIG. 5 is a flow diagram illustrating an exemplary operation of IMD 12 according to a learning mode. Specifically, FIG. 5 illustrates an exemplary mode of IMD 12 to learn a therapy for an event that is indicated by patient 14. Processor 34 enters the learning mode in response to receiving a command from patient 14 (70). Patient 14 may direct processor 34 to enter the learning mode by pressing a key of keypad 24 of programming device 20.

When operating in the learning mode, processor 34 defines an event 52 by receiving an indication from patient 14 (72). Patient 14 may indicate the event by, for example, pressing a key of keypad 24 that patient will thereafter use to identify the event to processor 34. The event 52 may be an activity and/or posture to be undertaken by patient 14, and the key may be used by patient 14 in the future to indicate to processor 34 that patient 14 is about to undertake the activity. Processor 34 may store information identifying the signal received by via telemetry circuit 38 when patient presses the key as the event 52 within memory 36.

Processor 34 then records therapy information, e.g., a learned therapy 54, while operating in the learning mode (74). As described above, the learned therapy 54 may be stimulation parameter values and/or one or more changes made to stimulation parameters by patient 14 over a period of time during operation within the learning mode. Processor 34 may store therapy information as a learned therapy at any time after receiving the command to enter the learning mode, e.g., before or after receiving an indication of the event from patient 14. Processor 34 stores the learned therapy 54 within memory 36, and associates the learned therapy 54 with the defined event 52 within memory 36 (76).

In exemplary embodiments, patient 14 adjusts stimulation parameters over a period of time after directing IMD 12 to enter the learning mode, e.g., during the event. For example, patient 14 may direct IMD 12 to enter the learning mode, so that IMD 12 learns appropriate adjustments to therapy to provide while patient 14 is running, and may adjust stimulation parameters while running to maintain effective and comfortable neuro stimulation therapy. IMD 12 may store the stimulation parameters and/or changes to the stimulation parameters and associate times with the parameters or changes, so that stimulation according to the parameters and changes to the stimulation may be provided at appropriate times during a subsequent occurrence of patient 14 running.

In other embodiments, rather than IMD 12 recording therapy information over time, patient 14 may use programming device 20 to enter a learned therapy 54 that includes time as a parameter. For example, patient 14 may create a learned therapy 54 for the "running" event that includes increases to pulse amplitude and width at particular time after the event is detected by IMD 12, and/or after N minutes that the event continues to be detected by IMD 12.

Figure 6:
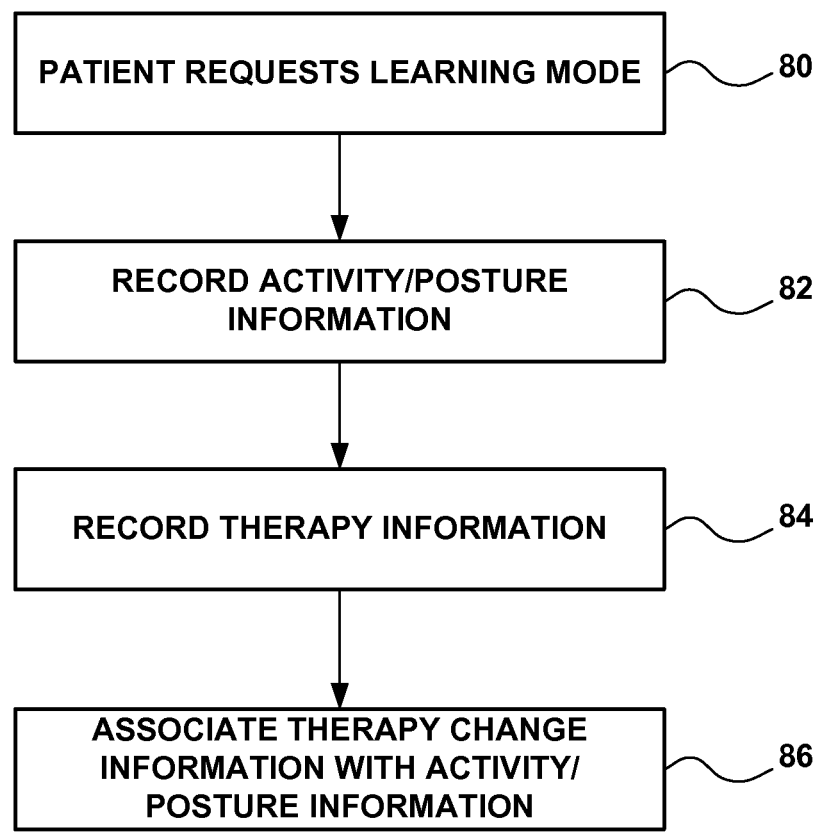
FIG. 6 is a flow diagram illustrating another exemplary operation of the medical device of FIG. 2 according to a learning mode.

FIG. 6 is a flow diagram illustrating another exemplary operation IMD 12 according to a learning mode. Specifically, FIG. 6 illustrates an exemplary mode of IMD 12 to learn a therapy for an event that that is defined by IMD 12 based on the output of a sensor 40. Processor 34 enters the learning mode in response to receiving a command from patient 14 (80).

While operating in the learning mode, processor 34 records at least one of the output of sensor 40 or the information provided by monitor circuit 42 based on the sensor output (82). Processor 34 may record the sensor output or information over any length of time, may record multiple samples, and may make the recording or recordings at any time after entering the learning mode. Processor 34 may store the recording(s), or the result of an analysis, e.g. feature, Fourier, or wavelet, or the recording(s) in memory 36 as an event 52. Processor 34 records therapy information as a learned therapy 54 during operation in the learning mode (84), and associates the learned therapy 54 with the defined event 52 (86), as described above with reference to FIG. 5.

Figure 7:
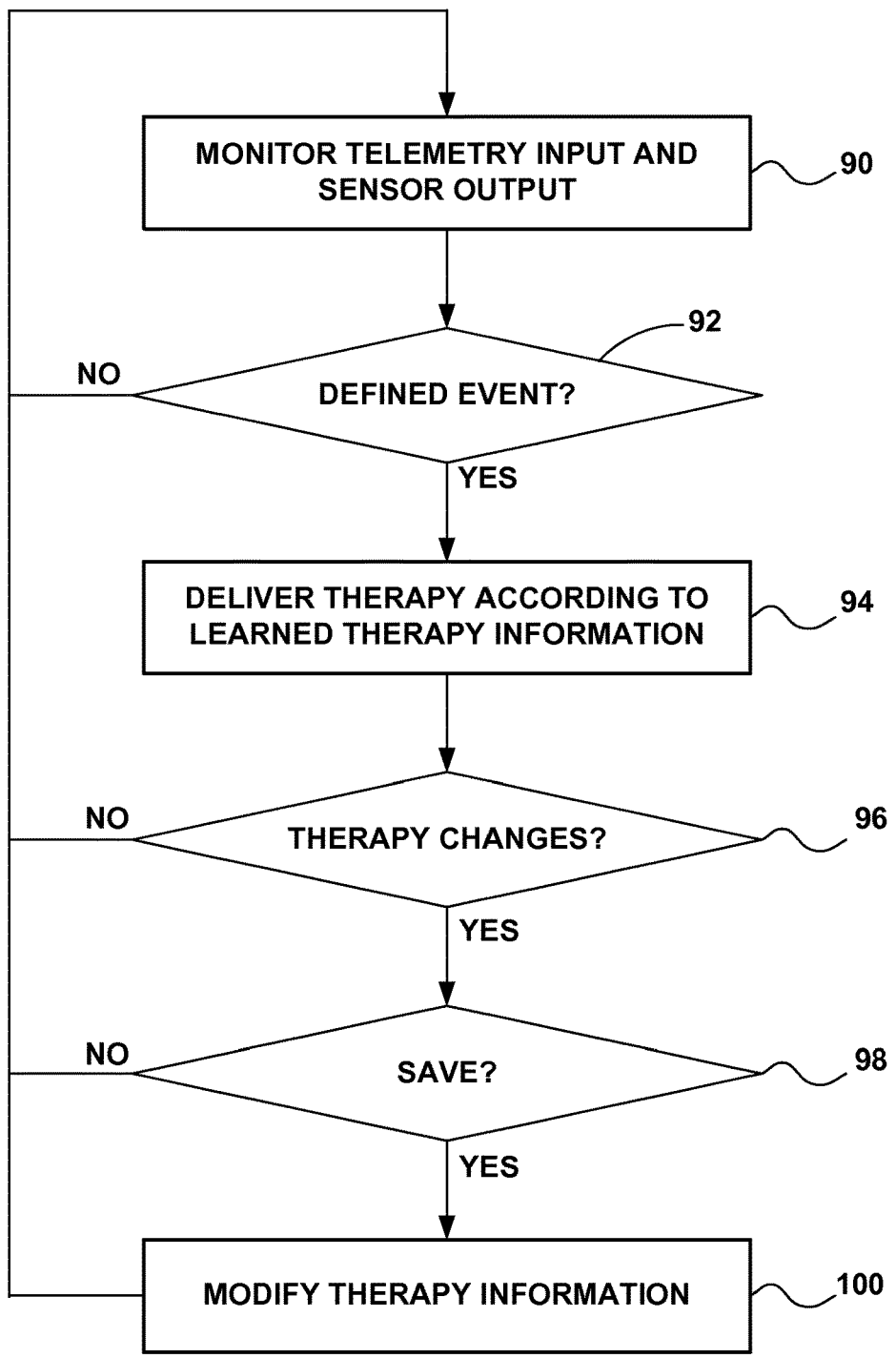
FIG. 7 is a flow diagram illustrating an exemplary operation of the medical device of FIG. 2 to provide discrete therapy adjustments according to the invention.

FIG. 7 is a flow diagram illustrating an exemplary operation of IMD 12 to provide automatic therapy adjustments according to the invention. Processor 34 monitors signals received from programming device 20 via telemetry circuit 38, and output of sensor 40 and/or monitor circuit 42, to detect previously defined events 52 (90). To monitor the sensor output, processor 34 compares the current sensor output to the event. 52. For example, processor 34 can compare the current sensor output to the sample sensor output recorded during operation in the learning mode, or the result of a signal analysis of the current sensor output to the result of a signal analysis of the sample sensor output recorded during operation in the learning mode. Processor 34 may use any of a variety of known pattern matching techniques or algorithms, such as fuzzy logic or neural network techniques or algorithms, to subsequently detect the previously defined events 52.

If processor 34 detects a previously defined event 52 (92), processor 34 controls therapy delivery circuit 32 to deliver therapy according to the learned therapy 54 associated with the detected event 52 in memory 36 (94). Processor 34 may control circuit 32 to deliver therapy according to parameter values of the learned therapy 54. Processor 34 may also control circuit 32 to change the parameter values over time according to the learned therapy 54.

If processor 34 detects that patient 14 has made changes to stimulation parameters during provision of therapy according to the learned therapy 54 (96), processor 34 may query patient 14 via programming device 20 as to whether the changes should be saved as a modification to the learned therapy 54 (98). If patient 14 wishes to save the changes, processor 34 modifies the learned therapy 54 according to the changes (100).

As described above, an event 52 may be an activity or posture undertaken by patient 14. For example, an event 52 may be patient 14 running, and the learned therapy 54 may include changes to stimulation parameters occurring at associated times during the "running" event such that effective and comfortable therapy is maintained. Other activities and postures that may affect the symptoms experienced by patient 14, or the effectiveness and side effects of the stimulation may include golfing, gardening, driving a car, sitting in a chair, twisting, or bending over. In some cases the duration of a particular activity or posture may affect the symptoms experienced by patient 14, or the effectiveness and side effects of the stimulation. In such cases an event 52 may be defined as occurring after patient 14 maintains an activity or posture for a defined duration.

In some cases, an activity or posture undertaken by patient 14 is results in an uncomfortable increase in the intensity of the stimulation delivered by IMD 12. This phenomenon is referred to as a "jolt.". Activities and postures that may lead to "jolts" include sitting in a seat, twisting, bending over, rapid posture changes, or other like postures or transitions between postures. Patient 14 may use the learning mode provided by IMD 12 as described herein to cause IMD 12 to define events 52 associated with the activities or postures that lead to "jolts," and associate such "jolt" events with therapy information 54 that causes IMD 12 to suspend or reduce the intensity of stimulation upon subsequent detection of the "jolt" events. Consequently, embodiments of IMD 12 may advantageously provide efficacious therapy during certain defined events 52, and avoid providing uncomfortable therapy during other defined events 52.

Figure 8:
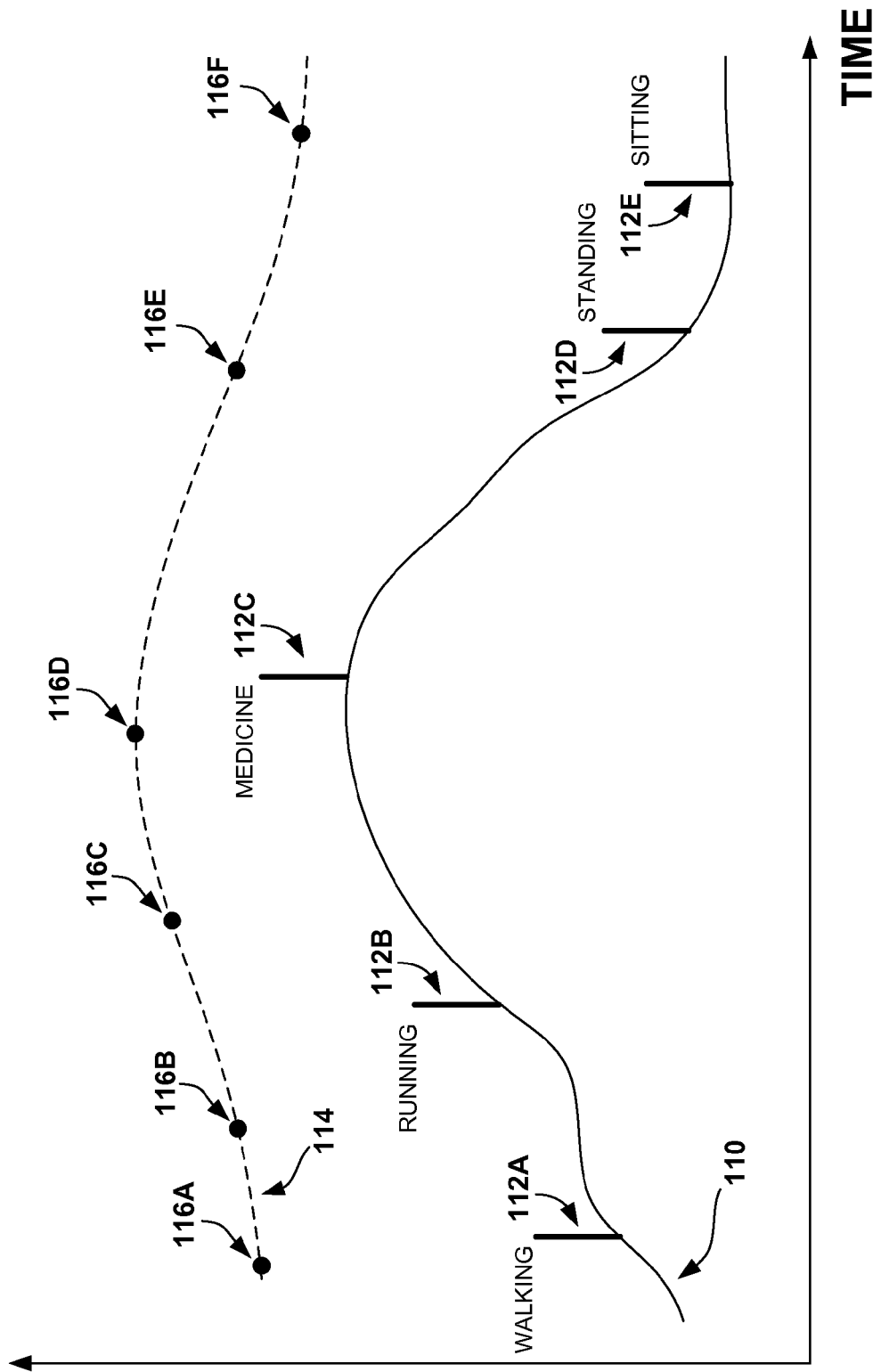
FIG. 8 is a timing diagram illustrating display of diagnostic information including learned events according to the invention.

FIG. 8 is a timing diagram illustrating display of diagnostic information 56 including learned events 52 according to the invention. As described above, in some embodiments processor 34 collects diagnostic information for review by a clinician that may include defined events, events indicated by patient 14 outside of the learning mode, the output of sensor 40 and/or monitor circuit 42, stimulation parameter values and/or changes made thereto over time, or the like. Diagnostic information 56 may be retrieved from IMD 12 by a clinician programmer and presented to a clinician in a variety of forms, such as the illustrated timing diagram, or various graphs, such as bar graphs, illustrating the result of a statistical analysis of diagnostic information 56. A clinician may use diagnostic data 56 to, for example, objectively assess patient activity, therapy effectiveness, patient compliance, or the like.

In the illustrated timing diagram, a curve 110 representing the activity level of patient 14, e.g., the output of one or both of sensor 40 and monitor 42, over time is displayed. Markers 112A-E are used to indicate the occurrence of events, which may be defined events 52. A second curve 114 illustrates the symptom, e.g., pain, intensity indicated by patient 14 over time. Curve 114 may be estimated based on intensity values 116A-F periodically entered by patient 14 using programming device 20.

Various embodiments of the invention have been described. However, one skilled in the art will appreciate that various modification may be made to the described embodiments without departing from the scope of the invention. For example, the invention is not limited to medical devices that deliver neurostimulation therapy or to implantable medical devices. Rather, systems that facilitate automatic therapy adjustment according to the invention may include one or more implantable or external medical devices, of any type, that deliver therapy to a patient. For example, in some embodiments, an implantable or external pump that delivers a therapeutic agent to a patient can provide automatic therapy adjustment according to the invention In some embodiments, a medical device that does not itself deliver therapy, such as a programming device, provides automatic therapy adjustment according to the invention. In such embodiments, the programming device may receive a command to enter a learning mode, an indication of an event, and therapy changes from the patient via a keypad, for example. The programming device may include a memory to store defined events and associated therapy information. When the user, e.g., the patient, again indicates occurrence of the event to the programming device via the keypad, the programming device controls a therapy delivery device to deliver therapy according to therapy information associated with the defined event.

The invention is not limited to embodiments wherein a programming device is a patient programmer. For example, in some embodiments, a programming device may be a clinician programmer used by a clinician to, for example, create the programs that control the delivery of therapy by a therapy delivery device. The clinician may use the clinician programmer, during a programming session for example, to cause the clinician programmer or the therapy delivery device to learn therapies for defined events as described herein In other embodiments, a system that facilitates automatic therapy adjustment does not include a programming device at all. Where a system includes an external medical device that provides therapy to a patient, for example, a user may interact with a user interface provided by the medical device and a programming device may therefore be unnecessary. A user may also interact with an implanted medical device using a magnetic activator, or by tapping over the implanted medical device, which may be detected via an accelerometer, as is known in the art. These and other embodiments are within the scope of the following claims.

The invention claimed is:

1. A method, comprising:
defining an event via at least one processor;
monitoring therapy delivered by a medical device during occurrence of the defined event, wherein monitoring comprises receiving, from a user, during a learning mode of the medical device, and during the occurrence of the defined event, therapy information indicative of changes made by the user to the therapy delivered by the medical device during the occurrence of the defined event;
associating the therapy information indicative of the monitored therapy with the defined event;
subsequently detecting, via a sensor, the defined event; and
providing subsequent therapy to a patient via the medical device according to the therapy information in response to the detection of the defined event.

2. The method of claim 1, wherein subsequently detecting the defined event comprises:
monitoring an output of the sensor; and
comparing the sensor output to the defined event.

3. The method of claim 2, wherein the sensor output reflects at least one of motion and posture of the patient.

4. The method of claim 1, wherein providing subsequent therapy to the patient comprises automatically making changes to the provided therapy over time based on the therapy information.

5. The method of claim 4, wherein the therapy information comprises information indicative of multiple changes to therapy parameters over time, and wherein providing subsequent therapy to the patient comprises automatically making changes to the provided therapy over time based on the therapy information.

6. The method of claim 5, wherein the therapy information comprises time information indicative of how the therapy parameters are to be changed over time, and wherein providing subsequent therapy to the patient comprises automatically making changes to the provided therapy over time based on the time information.

7. The method of claim 1, wherein defining the event comprises sensing a signal reflecting a physiological parameter of a patient and wherein receiving, from the user and during the occurrence of the defined event, therapy information indicative of changes to therapy delivered by the medical device comprises receiving, from the user, therapy information indicative of changes made by the user to therapy delivered by the medical device while sensing the signal reflecting the physiological parameter of the patient.

8. The method of claim 1, wherein receiving, from the user, during the learning mode of the medical device, and during the occurrence of the defined event, therapy information indicative of changes made by the user to therapy delivered by the medical device comprises recording a change to the monitored therapy during the occurrence of the defined event and wherein associating therapy information indicative of the monitored therapy comprises associating therapy information indicative of the recorded change to the monitored therapy with the defined event.

9. The method of claim 8, wherein receiving, from the user, during the learning mode of the medical device, and during the occurrence of the event, therapy information indicative of changes made by the user to therapy delivered by the medical device comprises recording a time of the change to the monitored therapy and wherein associating therapy information indicative of the monitored therapy comprises associating therapy information indicative of the recorded time of the change to the monitored therapy with the defined event.

10. The method of claim 9, wherein providing subsequent therapy to the patient comprises automatically changing the provided therapy according to the therapy information indicative of the recorded change and at a time determined by the therapy information indicative of the recorded time of the change.

11. The method of claim 1, wherein receiving, from the user, during the learning mode of the medical device, and during the occurrence of the event, therapy information indicative of changes made by the user to therapy delivered to the patient comprises receiving multiple changes to the therapy over time during the occurrence of the defined event and wherein associating therapy information indicative of the monitored therapy comprises associating therapy information indicative of the multiple changes to the therapy over time with the defined event.

12. The method of claim 1, wherein the medical device comprises an implantable medical device, and wherein receiving, from the user, during the learning mode of the medical device, and during the occurrence of the event, therapy information indicative of changes made by the user to therapy delivered by the medical device during the occurrence of the defined event comprises receiving user input to control the monitored therapy via a programming device.

13. The method of claim 1, wherein associating therapy information indicative of the monitored therapy with the defined event comprises associating therapy information indicative of multiple therapy parameter values with the defined event.

14. The method of claim 1,
wherein defining the event via at least the one processor comprises defining the event during an initial occurrence of the event, and
wherein receiving, from the user, during the learning mode of the medical device, and during the occurrence of the defined event, therapy information indicative of the changes made by the user to the therapy delivered by the medical device comprises receiving, from the user, during the learning mode of the medical device, and during the occurrence of the initial occurrence of the event, therapy information indicative of the changes to the therapy during the initial occurrence of the event.

15. The method of claim 1, further comprising, subsequent to defining the event, receiving input from the user to indicate that the event is about to occur.

16. The method of claim 15, wherein the event is a patient activity, and wherein receiving the input from the user indicates the patient is about to undertake the activity.

17. The method of claim 1, wherein providing subsequent therapy to a patient via the medical device according to the therapy information comprises receiving input from the user to change the therapy information.

18. The method of claim 1, wherein defining the event comprises defining the event to occur after the patient maintains an activity or posture for a predefined duration.

19. A medical device, comprising:
a therapy delivery module configured to deliver therapy to a patient;
a sensor configured to generate an output; and
a processor configured to:
 define an event;
 monitor delivery of the therapy delivered during occurrence of the defined event, wherein to monitor, the processor is configured to receive, from a user, during a learning mode of the medical device, and during occurrence of the defined event, therapy information indicative of changes made by the user to therapy delivered during the occurrence of the defined event;
 associate the therapy information indicative of the monitored therapy with the defined event;
 detect, via the output of the sensor, the defined event; and
 control delivery of subsequent therapy to the patient according to the therapy information in response to the detection of the defined event via the sensor.

20. The medical device of claim 19, wherein the processor is further configured to detect the defined event by monitoring an output of the sensor and comparing the sensor output to the defined event.

21. The medical device of claim 20, wherein the sensor is configured to provide an output that reflects at least one of motion and posture of the patient.

22. The medical device of claim 19, wherein the processor is configured to control delivery of subsequent therapy to the patient by automatically making changes to the delivered therapy over time based on the therapy information in response to detecting the defined event.

23. The medical device of claim 22, wherein the processor is configured to associate the therapy information with the defined event that comprises information indicative of multiple changes to therapy parameters over time, and wherein the processor is configured to control delivery of subsequent therapy to the patient by automatically making changes to the delivered therapy over time based on the therapy information.

24. The medical device of claim 23, wherein the processor is configured to associate the therapy information with the defined event that comprises time information indicative of how the therapy parameters are to be changed over time, and wherein the processor is configured to control delivery of subsequent therapy to the patient by automatically making changes to the delivered therapy over time based on the time information.

25. The medical device of claim 19, wherein the sensor is configured to provide an output that reflects a physiological parameter of the patient, and wherein the processor is configured to receive, from the user, during the learning mode of the medical device, and during the occurrence of the defined event, therapy information indicative of changes made by the user to therapy delivered by the medical device by receiving, from the user, during the learning mode of the medical device, and during the occurrence of the defined event, therapy information indicative of changes made by the user to therapy delivered by the medical device while monitoring the output of the sensor that reflects the physiological parameter of the patient.

26. The medical device of claim 19, wherein the processor is configured to receive, from the user, during the learning mode of the medical device, and during the occurrence of the event, therapy information by recording a change to the monitored therapy while sensing the signal and to associate therapy information indicative of the recorded change to the monitored therapy with the defined event.

27. The medical device of claim 26, wherein the processor is configured to receive, from the user, during the learning mode of the medical device, and during the occurrence of the event, therapy information by recording a time of the change to the monitored therapy and to associate therapy information indicative of the recorded time of the change to the monitored therapy with the defined event.

28. The medical device of claim 27, wherein the processor is configured to control delivery of subsequent therapy to the patient by automatically changing the delivered therapy according to the therapy information indicative of the recorded change and at a time determined by the therapy information indicative of the recorded time of the change.

29. The method of claim 19, wherein the processor is configured to receive, from the user, during the learning mode of the medical device, and during the occurrence of the event, therapy information by receiving multiple changes to the therapy over time while sensing the signal and to associate therapy information indicative of the multiple changes to the therapy over time with the defined event.

30. The medical device of claim 19, wherein the medical device is an implantable medical device, and further comprising a telemetry module configured to receive user input to control the delivery of subsequent therapy during occurrence of the defined event.

31. The medical device of claim 19, wherein the processor is configured to associate therapy information indicative of multiple therapy parameter values with the defined event.

32. The medical device of claim 19, wherein the processor is configured to receive input from the user subsequent to defining of the event to indicate that the event is about to occur.

33. The medical device of claim 32, wherein the event is a patient activity, and wherein receiving the input from the user indicates the patient is about to undertake the activity.

34. The medical device of claim 19, wherein the processor is configured to receive input from the user while controlling delivery of subsequent therapy to the patient, the input being provided to change the therapy information.

35. The medical device of claim 19, wherein the processor is configured to define the event to occur after the patient maintains an activity or posture for a predefined duration.

36. A medical system, comprising:
a medical device, comprising:
a therapy delivery module configured to deliver therapy to a patient; and
a sensor configured to generate an output; and
one or more processors configured to:
define an event;
monitor delivery of the therapy delivered by the medical device during occurrence of the defined event, wherein to monitor, the one or more processors are configured to receive, from a user, during a learning mode of the medical device, and during the occurrence of the defined event, therapy information indicative of changes made by the user to the therapy delivered during the occurrence of the defined event;
associate the therapy information indicative of the monitored therapy with the defined event;
detect, via the output of the sensor, the defined event; and
control delivery of subsequent therapy to the patient according to the therapy information in response to the detection of the defined event via the sensor.

37. The medical system of claim 36, wherein the one or more processors comprises a processor external to the patient.

38. The medical system of claim 36, wherein the one or more processors comprises a processor implanted in the patient.

39. The medical system of claim 36, further comprising a programmer configured to communicate telemetrically with at least one of the one or more processors.

40. A non-transitory computer readable storage medium storing instructions to cause a programmable processor of a medical device to:
define an event;
monitor therapy delivered by a medical device during occurrence of the defined event, wherein the instructions that cause the programmable processor to receive comprise instructions that cause the programmable processor to receive, from a user, during a learning mode of the medical device, and during the occurrence of the defined event, therapy information indicative of changes made by the user to therapy delivered by the medical device during the occurrence of the defined event;
associate therapy the information indicative of the monitored therapy with the defined event;
subsequently detect, via a sensor, the defined event; and
provide subsequent therapy to a patient via the medical device according to the therapy information in response to the detection of the defined event.

41. A system, comprising:
means for defining an event;
means for monitoring therapy delivered by a medical device during occurrence of the defined event, wherein the means for monitoring comprises means for receiving, from a user, during a learning mode of the medical device, and during the occurrence of the defined event, therapy information indicative of changes made by the user to therapy delivered by the medical device during the occurrence of the defined event;

means for associating the therapy information indicative of the monitored therapy with the defined event;

means for subsequently detecting the defined event; and means for providing subsequent therapy to a patient according to the therapy information in response to the detection of the defined event.

\* \* \* \* \*